United States Patent
Spotorno et al.

(10) Patent No.: US 6,319,256 B1
(45) Date of Patent: Nov. 20, 2001

(54) BONE RASP FOR A FEMUR HEAD PROSTHESIS

(75) Inventors: Lorenzo Spotorno, Finale Ligure (IT); Markus Lechner, Zürich (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/502,556

(22) Filed: Feb. 10, 2000

(30) Foreign Application Priority Data

Mar. 4, 1999 (EP) .................................................. 99810186

(51) Int. Cl.[7] .................................................. A61B 17/88
(52) U.S. Cl. .................................................. 606/85; 606/79
(58) Field of Search .................................................. 606/85, 84, 82, 606/80, 81, 92, 95, 99, 100, 176, 177, 178, 179; 132/76.4, 76.5; 408/227, 228, 229, 230, 231

(56) References Cited

U.S. PATENT DOCUMENTS

| 4,765,328 | * | 8/1988 | Keller et al. | 606/85 |
| 4,921,493 | | 5/1990 | Webb, Jr. | |
| 5,454,815 | * | 10/1995 | Geisser et al. | 606/85 |
| 5,665,091 | * | 9/1997 | Noble et al. | 606/85 |
| 5,931,841 | * | 8/1999 | Ralph | 606/85 |

FOREIGN PATENT DOCUMENTS

| 0378044A1 | 7/1990 | (EP) . |
| 0563585A1 | 10/1993 | (EP) . |

* cited by examiner

*Primary Examiner*—Pedro Philogene
(74) *Attorney, Agent, or Firm*—Townsend and Townsend and Crew LLP

(57) ABSTRACT

A bone rasp has an elongate body which tapers in the distal direction with first cutting ribs which extend transversely to the longitudinal axis of the body and are arranged in parallel graduations at a first spacing along the longitudinal axis and with second cutting ribs which are formed in parallel graduations at a second spacing at the body. The first and second cutting ribs have a different depth of cut in order to ablate different amounts.

14 Claims, 2 Drawing Sheets

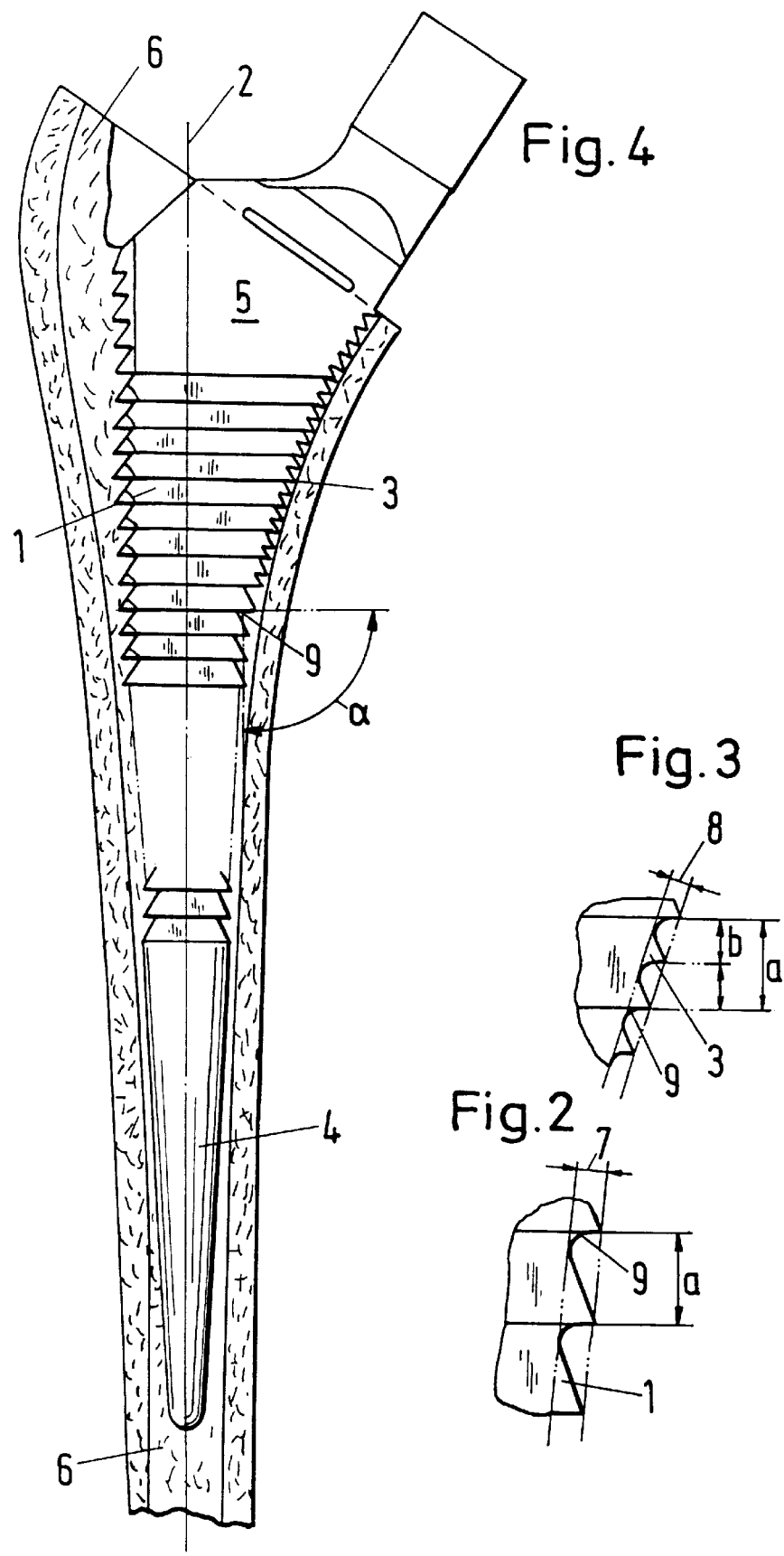

BONE RASP FOR A FEMUR HEAD PROSTHESIS

Figure 1:
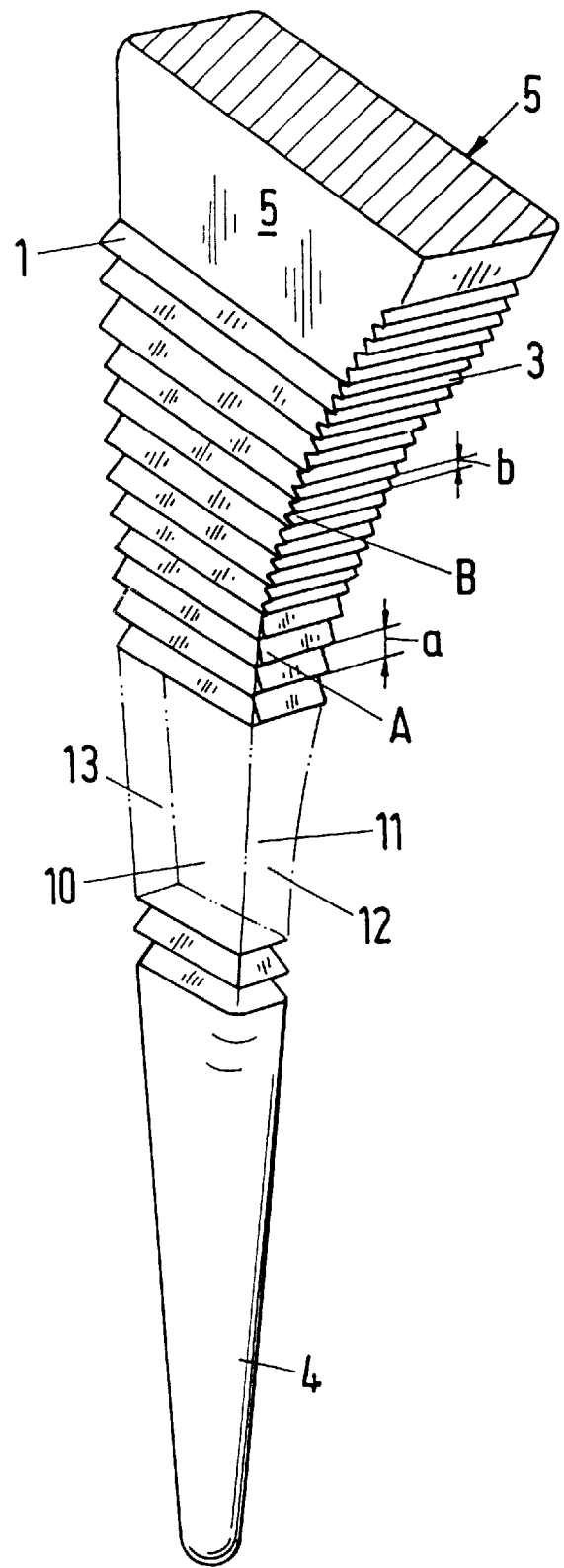

The invention relates to a bone rasp for a femur head prosthesis in accordance with the preamble of claim 1.

The known rasps have an elongate, conical body with a rectangular cross-section. Cutting ribs are formed at the body which are arranged transversely to the longitudinal axis of the body and which have the same cross-sectional shape and dimensions.

In the use of the rasp, substantially the same amount is ablated over the whole length. In this it proves disadvantageous that in regions with greater cone angle in particular an excess amount is ablated or a blocking of the rasp takes place, although it has not yet centered itself through forces acting at all sides. For a surgeon it is therefore difficult to correctly interpret the resistance of the rasp on hammering it in.

The invention, as is characterised in the claims, satisfies the object of improving a bone rasp for a femur prosthesis.

One property lies in that for a given cutting rib geometry the shaving space decreases over-proportionally at smaller cutting rib spacing. The shaving spaces between the cutting ribs with small spacing, which are provided at locations with a greater cone angle, fill up relatively rapidly and prevent too great a local ablation. When the rasp is hammered in, the forces arising radially at the rasp equalise one another in such a manner that a self-guiding arises in the marrow chamber in which the relatively thin-walled corticalis remains medially in the proximal part.

In contrast to hollow rasps with an excessively large chip space, the bone chips are not carried out of the marrow chamber due to the intentionally adapted undercuttings, but rather are thrust deeper with each new hammering in and compressed in the regions which do not lie in contact with the rasp until the rasp has a full peripheral contact with cut open or with compressed bone matter.

In the following the invention will be explained with reference to the accompanying drawings.

Shown are:

FIG. 1 a view of an embodiment of a bone rasp in accordance with the invention;

FIG. 2 a detail A in FIG. 1;

FIG. 3 a detail B in FIG. 1 and

FIG. 4 a view of a further embodiment of a bone rasp which is inserted in a femur bone.

The bone rasp under discussion here corresponds in shape practically to a femur prosthesis so that a prosthesis can be directly inserted or cemented in into the prepared cavity.

In the case of directly inserted prostheses the associated bone rasp can have an under-dimensioning in the region of longitudinal ribs of the prosthesis which corresponds for example to half the rib height of the prosthesis. Depending on the configuration of the longitudinal ribs, an under-dimensioning of 20% to 70% is conceivable.

FIG. 1 shows a rasp with an elongate body, the side surfaces 10, 11, 12, 13 of which substantially form a rectangular cross-section and which tapers in the direction towards the distal end, comprising a plurality of first cutting ribs 1 which are arranged at the body in parallel gradations in the direction of the longitudinal axis transversely to the longitudinal axis 2 and at a first spacing a, comprising second cutting ribs 3 which are formed parallel to one another at a second spacing b at least at one side surface of the body and comprising a section 4 which is formed at the distal end and is provided with a smooth surface. The first cutting ribs 1 are formed at the lateral and medial side as well as at the posterior and anterior side of the body. The second cutting ribs 3 are formed at the medial side of the body in the region with the greater cone angle. As can be seen in FIGS. 2 and 3 the spacings of the second cutting ribs 3 are smaller than the spacings of the first cutting ribs 1. A spacing b is advantageously chosen for the second cutting ribs 3 which corresponds to a fraction of the spacing a of the first cutting ribs 1 with an integral reciprocal value, e.g. ½, ⅓. Thus the first and the second cutting ribs 1 and 3 have, in the presence of a similar geometry, a different depth of cut 7, 8 which is in addition variable through the choice of the backoff angle so that different amounts are ablated. In the proximal region, sections 5 with smooth surface are provided in each case on the posterior and the anterior side.

For a better understanding of the invention a femur bone is illustrated in FIG. 4 in which a rasp of this kind is inserted. During the insertion of the rasp into the cavity in the bone 6 a pre-orientation takes place through the section 4 at the distal end. During the hammering in of the rasp, material is ablated through the cutting grooves 1 and 3, with less material being ablated at the medial side in the region of the greater cone angle. Here the rasp is guided at the medial side, through which the hammering in is simplified. The material which is ablated by the cutting grooves 1 and 3 is compressed at the distal end of the rasp by the section 4 or at the proximal end of the rasp by the sections 5. A monitoring ball (not illustrated) can be placed onto the rasp for checking the position of the prosthesis to be inserted with respect to the hip shell. After the rasp is removed a femur head prosthesis can be directly inserted or cemented in into the prepared cavity.

The guiding during the cutting and the release of chipped material during the hammering out of the rasp can be varied in addition through the variation of the cutting angle $\alpha$ of the cutting surfaces 9 with respect to the longitudinal axis 2 of the rasp and through a variation of the backoff angle of the cutting ribs 1, 3. Thus for example with a cutting angle $\alpha > 90°$, less is cut and more is compressed, whereas with a reduction of the backoff angle through a reduction of the chip space the amount cut is limited and more easily given off during the withdrawal.

In this way it is possible afterwards to allow a zone with second cutting ribs 3 on all sides which compress more than cut to border on the distal smooth section 4.

What is claimed is:

1. A bone rasp for a femur head prosthesis comprising an elongate body which tapers in a distal direction, side surfaces of which form a substantially rectangular cross-section, and comprising a plurality of first cutting ribs which extend transversely to the longitudinal axis of the body and are arranged in parallel graduations at a first spacing along the longitudinal axis, wherein second cutting ribs are formed in parallel graduations at a second spacing at most at three side surfaces of the body, with the first and second cutting ribs having a different depth of cut in order to ablate different amounts.

2. The bone rasp in accordance with claim 1 wherein the first and second cutting ribs being arranged group-wise.

3. The bone rasp in accordance with claim 1 wherein the second cutting ribs being arranged at a medial side of the body in the region of the greater cone angle.

4. The bone rasp in accordance with claim 1 wherein the second spacing being smaller than the first spacing.

5. The bone rasp in accordance with claim 1 wherein the second cutting ribs having a lesser depth of cut than the depth of cut of the first cutting ribs.

6. The bone rasp in accordance with claim 1 wherein the cutting edges of a group of cutting ribs forming a cutting angle greater than 90° with the longitudinal axis.

7. The bone rasp in accordance with claim 4 wherein the second spacing being a fraction of the first spacing, a reciprocal value of which corresponds to a whole number.

8. The bone rasp in accordance with claim 1 wherein the cutting ribs displaced with respect to one another in the direction of the longitudinal axis from one side surface to an adjacent side surface.

9. The bone rasp in accordance with claim 1 wherein a section at the distal end which is provided with a smooth surface.

10. The bone rasp in accordance with claim 1 wherein a proximal region comprising a posterior and anterior side wherein each case a section with a smooth surface is provided.

11. The bone rasp in accordance with claim 9 wherein a zone with first cutting ribs on all sides borders on above the smooth distal section.

12. A prosthesis system consisting of a bone rasp, the bone rasp comprising an elongate body which tapers in a distal direction, side surfaces of which form a substantially rectangular cross-section, the system further comprising a femur head prosthesis with longitudinal ribs, which is provided for an insertion after the rasping of a bone bed, whereby the rasp is provided with an under-dimensioning of 20% to 70% of the rib height in regions in which the prosthesis has longitudinal ribs.

13. A bone rasp for a femur head prosthesis comprising an elongate body which at all sides tapers continuously in a distal direction, side surfaces of which form a substantially rectangular cross-section, and comprising a plurality of first cutting ribs which extend transversely to the longitudinal axis of the body and are arranged in parallel graduations at a first spacing along the longitudinal axis, comprising a section at the distal end which has a smooth surface and which takes about one quarter or more of the length of the elongate body and comprising at a proximate end of the elongate body a posterior and anterior side each having a section with a smooth surface for compressing bone tissue.

14. A bone rasp in accordance with claim 13 having second cutting ribs (3) formed in parallel graduations at a second spacing at least at one side surface of the body, wherein the first and second cutting ribs having a different depth of cut in order to ablate different amounts.

* * * * *